United States Patent [19]

Gerke et al.

[11] Patent Number: 5,375,459
[45] Date of Patent: Dec. 27, 1994

[54] DEFOAMER TESTING APPARATUS

[75] Inventors: Richard Gerke, Charlotte, N.C.; José M. Rodriguez, Fort Mill, S.C.; John J. Palmer, Monroe, N.C.

[73] Assignee: Henkel Corporation, Plymouth Meeting, Pa.

[21] Appl. No.: 166,191

[22] Filed: Dec. 13, 1993

[51] Int. Cl.$^5$ .............................. G01N 13/00
[52] U.S. Cl. .................................. 73/60.11
[58] Field of Search ............... 73/60.11, 61.43, 61.41

[56] References Cited

U.S. PATENT DOCUMENTS 3,107,519 10/1963 McGinn .................................. 73/53

Primary Examiner—Hezron E. Williams
Assistant Examiner—Michael J. Brock
Attorney, Agent, or Firm—Ernest G. Szoke; Wayne C. Jaeschke; Real J. Grandmaison

[57] ABSTRACT

An apparatus and method is provided wherein the foam inhibiting effectiveness of defoaming and antifoaming additives on various types of foamable liquid mediums is measured. A single generally cylindrical foam cell having openings at both ends is provided wherein an interchangeable foam cell insert having varied geometry is longitudinally disposed within the foam cell. The foam cell insert is provided with a plurality of centralizer walls extending into the foam cell with an agitator member being carried by the centralizer walls. Foamable liquid medium is introduced into the foam cell and recirculated therethrough to form a dynamic fluid-flow system. As the liquid medium passes through both the foam cell and the foam cell insert, it comes into contact with the agitator member carried by the centralizer walls of the foam cell insert forming foam which accumulates in the foam cell. After a sufficient amount of foam is formed, a defoaming or antifoaming agent is introduced into the foam cell, and its effect on the level of foam present in the foam cell is measured. The interchangeable foam cell inserts are of varying lengths and carry varyingly configured agitator members, so that depending on whether a high or low foaming liquid medium is introduced, an appropriate foam cell insert may be chosen and inserted into the foam cell. The interchangeable foam cell inserts allow for a single foam cell to be used for measuring purposes thus decreasing the cost and potential down-time associated with such testing.

24 Claims, 5 Drawing Sheets

DEFOAMER TESTING APPARATUS

FIELD OF THE INVENTION

The present invention generally relates to a method and apparatus for testing the foaming characteristics of various liquid mediums. More particularly, the invention relates to an improved method and apparatus for measuring the effectiveness of defoamer and antifoam additives on liquid mediums having varying degrees of foaming abilities using a single foam cell provided with interchangeable inserts thereby eliminating the necessity of employing multiple foam cells.

BACKGROUND OF THE INVENTION

Various industries utilize chemicals which, when used in a particular application have a tendency to foam. This foaming phenomenon is oftentimes an undesirable by-product associated with the use of these chemicals, and its presence may have detrimental consequences. In an effort to try and combat this foaming phenomenon, various defoamers and antifoam additives have been formulated which either reduce the amount of foam formed or knock-down the foam at a specific point in the process.

Companies which manufacture and market these defoamers and antifoam additives have become aware of the importance of good bench testing for determining the effectiveness of their products. A good bench test is one which most closely simulates the environment or conditions under which these defoaming or antifoaming additives will be employed, i.e., the customer's process or application. In many industries, such as pulp and paper, defoamers are used as production aids in the respective processes. In these types of applications, defoamer or antifoam additives are employed to maximize productivity and insure against quality problems. These additives, though they do contribute to the cost associated with the particular process, are nevertheless less expensive than the cost of waste stemming from a loss in production capacity or inferior quality of the product formed. Due to the importance of these types of additives in specific processes, defoamer and antifoam users are generally reluctant to experiment with different additives in their processes. The possible benefit which may be derived by employing an improved additive oftentimes fails to outweigh the potential cost of problems if the additive proves ineffective. As a result, bench test methods must be used to assess the performance of any new additive prior to it being recommended to a potential user. A good bench test is a crucial component of new product development, quality control, i.e., fitness for use, and product improvement. These bench tests are also a useful marketing tool in trying to convince a potential user to employ an existing additive or an existing user to employ an improved additive. They serve to demonstrate to a customer that a particular additive will perform effectively in their specific process.

A foam testing apparatus is most often used to perform the above-mentioned bench tests. Defoamer and antifoam additive sales personnel usually carry a defoamer test kit which is capable of testing the effectiveness of an additive in the field. These portable test kits are an invaluable sales tool for they enable the prospective user to see the effectiveness of the additive on various types of foamable liquids. One particular type of defoamer test kit is known as a foam cell. With this type of apparatus, a recirculating fluid flows into and out of the foam cell, whereby the agitation of the fluid in the foam cell causes the fluid to foam. The foam cell is provided with a graduated scale for measuring the height of the foam within the cell. Once a sufficient amount of foam is formed in the cell, i.e., a visually acceptable amount, a defoaming or antifoaming additive is then introduced into the cell. Measurements are then taken to determine the effect of the additive on the foam at the point of introduction, and shortly thereafter, by visually measuring the foam height within the cell.

One type of foam testing apparatus known as an annular foam cell that is used in the industry is disclosed in U.S. Pat. No. 3,107,519, comprising a measuring cylinder open at the top and having a discharge at the bottom. A foam cup, shorter and of smaller diameter than the cylinder, is disposed therein. A long slender tube extends at one end into the cup, with its other end being connected to the outlet of a recirculating pump. In operation, a measured quantity of liquid is continuously pumped into the foam cup causing both the liquid and resultant foam which is formed to spill into the cylinder. Once an adequate amount of foam has been formed, a defoaming additive is then deposited into the cylinder. The effectiveness of the defoamer is determined by measuring the initial drop in foam level, and suppression of further foam formation over a predetermined amount of time.

It has been observed that the afore-mentioned foam testing apparatus has certain deficiencies. For example, it is difficult to accommodate a wide variety of process liquids having varying degrees of foaming ability in one apparatus or employing one test method. These types of liquids are referred to in the industry as high foaming and low foaming liquids. According to the above-cited patent, the testing of these types of liquids requires the further use of an aspirator, if necessary, located in the line just above the entrance to the tube to increase foam generation, or throttling the recirculation rate to reduce the rate of foam generation. Increasing the flow rate of low foaming liquids to generate foam helps the evaluation process, but there is a practical limit to the amount of flow the cell can accommodate. A nozzle or aspirator has limited benefit because of the severe restrictions it imposes on the recirculation flow rate. In other situations, the foaming process medium is too foamy for the foam test apparatus of the prior art. Reducing the circulation flow rate makes the system slower to react and diminishes the benefit of an annular foam cell design. Thus, it would be advantageous to have a better means of adapting a foam cell apparatus to optimize foam generation rates for different foaming media enabling comparison thereof.

Other types of foam testing apparatus utilize two separate foam cylinders to measure the effectiveness of defoaming additives on high and low foaming liquids. One cylinder is specifically ! designed to accommodate high foaming liquids, while the other is designed to promote foaming of low foaming liquids. The disadvantages associated with such test kits are obvious. The cost of putting together such a test kit is significantly increased, for now two foam cells have to be employed. Also, the potential for breakage, coupled with the resultant down-time of the testing system, is now doubled.

Therefore, it would be advantageous, and it is a primary object of this invention to provide an apparatus with an improved foam cell wherein a single cell can be employed to test the effectiveness of both high and low foaming liquids.

A related phenomenon known as entrained air has been found to be just as, if not more, detrimental to industrial processes as foaming. Defoamer and antifoam additives are also used to dissipate any entrained air which manifests itself during industrial processes. It has been found that by employing an in-line density sensor in combination with the foam testing apparatus of this invention, it is possible to measure the effectiveness of these additives relative to both foam and entrained air dissipation. The in-line density sensor offers the advantage of being capable of quantifying entrained air in addition to, or in place of visual surface foam measurements. This system allows for relatively easy automation of density data since the density sensor is a microprocessor based instrument.

Therefore, it is yet another object of this invention to provide an improved method and apparatus for measuring the effectiveness of defoamer and antifoam additives on entrained air formed during a particular process.

SUMMARY OF THE INVENTION

Briefly stated, the present invention relates to an apparatus for measuring the effectiveness of various defoaming and antifoaming agents. The apparatus comprises a generally cylindrical foam cell having a graduated scale located thereon and an inlet port located at one end for receiving a foamable liquid medium and an outlet port distally located from the inlet port for discharging the liquid medium, wherein the foamable liquid medium is first introduced into and then recirculated through the foam cell, after which a defoaming or antifoaming agent is then introduced into the cell for evaluation of its foam inhibiting effectiveness. Interchangeable foam cell inserts, of varied geometry, removably mounted over the inlet port of the foam cell, are disposed within the foam cell. The foam cell inserts comprise a plurality of centralizer walls extending longitudinally within the cell along a central axis of rotation of the cell. A liquid agitating member is carried by the centralizer walls of the foam cell insert which promotes the formation of foam when the liquid comes into contact with the agitating member. Liquid supply means provide a foamable liquid medium to the foam cell, after which the liquid medium is then discharged through the outlet port and continuously recirculated back into the foam cell by liquid delivery means, thus forming a dynamic foam system. The length and diameter of the foam cell insert varies depending on the type of foamable liquid medium being employed. Similarly, the agitating member has varying configurations which also correspond to the particular foam cell insert to be employed. Hence, depending on the particular type of foamable liquid medium to be tested, i.e., low foaming or high foaming, the appropriate foam cell insert is employed. A terminal end of the foam cell insert is positioned a predetermined distance above the outlet port of the foam cell, this distance also being dependent on the particular foam cell insert chosen.

According to the method aspect of the invention, an interchangeable foam cell insert of appropriate geometry is selected, depending on the type of foamable liquid medium being employed. The foam cell insert is then removably mounted onto the inlet port of a generally cylindrical foam cell. The foam cell insert is provided with a plurality of centralizer walls which extend longitudinally into and are thus disposed within the foam cell. An agitating member is also provided which is carried by the centralizer walls of the foam cell insert. A foamable liquid medium is then introduced into, and continuously recirculated through, the foam cell. Foam is formed when the liquid medium passes through both the foam cell and foam cell insert and comes into contact with the agitating member of the foam cell insert. After a sufficient amount of foam is formed, but while the liquid medium continues to be recirculated through the foam cell to provide a dynamic fluid environment, a defoaming or antifoaming agent is then introduced into the foam cell and its effect on the foam present therein is evaluated by measuring the drop in foam level within the foam cell using a graduated scale present on the foam cell.

BRIEF DESCRIPTION OF THE DRAWINGS

The foregoing summary, as well as the following detailed description will be better understood when read in conjunction with the appended drawings. For the purpose of illustrating the invention, there is shown in the drawings embodiments which are presently preferred, it being understood however, that this invention is not limited to the precise arrangement and instrumentalities shown.

DETAILED DESCRIPTION OF THE INVENTION

Figure 1:
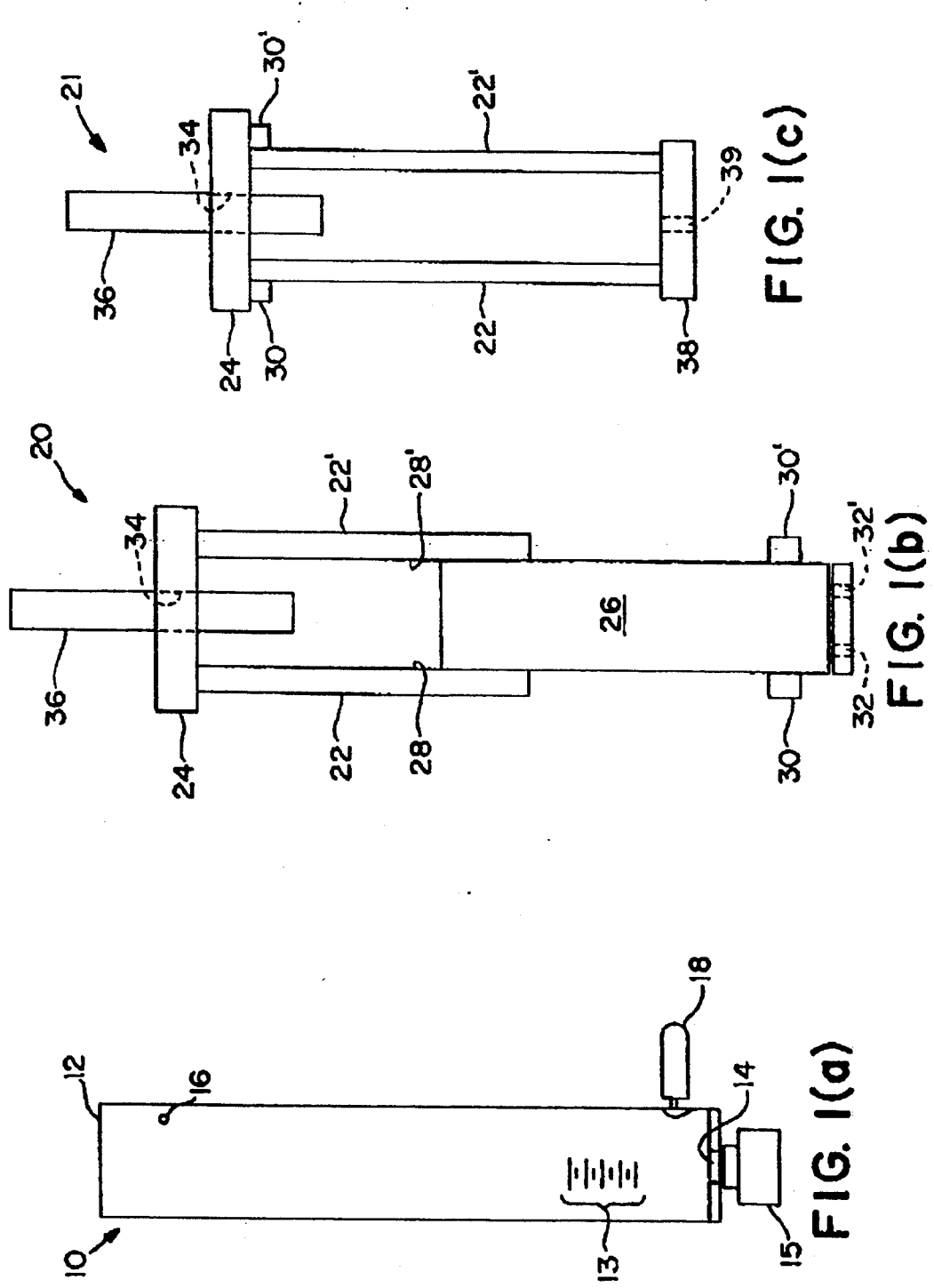
FIG. 1(a) is a side elevational view of a generally cylindrical foam cell into which interchangeable foam cell inserts are disposed.
FIG. 1(b) is a side elevational view of one embodiment of a foam cell insert adapted for use in testing low foam generating liquids.
FIG. 1(c) is a side elevational view of another embodiment of the foam cell insert adapted for use in testing high foam generating liquids.

Referring to the drawings, wherein like numerals indicate like elements throughout, there is shown in FIG. 1(a) a cylindrical foam cell referred to generally by reference numeral 10. The cell 10 is provided with an inlet port 12 for receiving a foamable liquid medium. At a distal end from said inlet port 12 is an outlet port 14 having an outlet conduit 15 connected thereto for discharging the foamable liquid medium as it passes through the foam cell, after which it is then recirculated back through the foam cell via the inlet port 12. A graduated scale 13 is provided on the .foam cell 10 for measuring the height of foam contained in foam cell 10. It should be noted, however, that any type of measuring means may be employed without departing from the spirit and scope of the invention.

In addition, the foam cell 10 is provided with an injection aperture 16 located at an upper end of foam cell 10 for introducing a defoaming or antifoaming agent into the foam cell 10 for evaluation. It should be noted, however, that any type of opening for introducing the defoaming agent to be tested can be provided anywhere along the foam cell without departing from the scope or spirit of the invention. Similarly, thermometer 18 may also be provided for measuring and/or controlling the temperature of the foaming liquid.

It should be noted that the geometry of foam cell 10 is variable with respect to its length and diameter, and is dependent on the particular foaming properties of the foamable liquid medium to be tested. For example, a longer more narrow foam cell may be employed in order to visually amplify foam being formed within foam cell 10. This type of construction is useful for taking either more precise measurements since a more precise graduated scale may be employed on foam cell 10, and/or a lower foaming liquid medium can be better tested since the amount of foam being formed will also be visually amplified within foam cell 10. The only geometrical constant that must be observed is that the inner diameter of foam cell 10 be greater than the outer diameter of foam insert 20 or foam insert 21 to be inserted therein.

There is shown in FIG. 1(b), one embodiment of a foam cell insert 20 for use in evaluating low foam generating liquids in accordance with the present invention. Substantially flat centralizer walls 22 and 22' are removably mounted onto the inlet port 12 of foam cell 10 so that centralizer walls 22 and 22' extend longitudinally into foam cell 10 along a central axis of rotation of the high foam generating cell insert 20. The length of the centralizer walls 22 and 22' may vary depending on the foaming properties of the foamable liquid medium being employed, i.e., high or low foaming. In this embodiment, the centralizer walls 22 and 22' are approximately 15 cm in length and are shown mounted onto the inlet port 12 of foam cell 10 via annular seat member 24, the seat member 24 being adapted to be removably attached to the inlet port 12 of the foam cell 10. The diameter of the seat member 24 is typically slightly greater than that of the inlet port 12 so that the seat member 24 is adapted to rest on the edges of the inlet port 12. In one embodiment, the diameter of the seat member is about 6.5 cm. The centralizer walls 22 and 22' are fixedly mounted to the seat member 24 so that the latitudinal distance between the centralizer walls 22 and 22' is less than the diameter of both the seat member 24 and foam cell 10, thus enabling centralizer walls 22 and 22' to be concentrically disposed within foam cell 10.

Seat member 24 is provided with annular opening 34 through which liquid may enter into both the foam cell 10 and foam cell insert 20. A spout member 36 is also shown for providing the efficient introduction of liquid medium into the test apparatus. The seat member 24 may also have multiple annular openings for venting purposes. It should be noted, however, that while an annular seat member is presently disclosed for supporting the foam cell insert 20 within foam cell 10, any other type of support means may also be employed, or none at all, if for example the insert is adapted to be frictionally secured within the foam cell wherein the centralizer walls 22 and 22' are in frictional contact with interior walls of foam cell 10, without departing from the scope or spirit of the invention.

In a preferred embodiment of a foam cell insert for use with low foam generating liquids (not shown), the foam cell insert 20 is about 30 cm in length and is provided with three centralizer walls spaced at 120 degree angles to each other, relative to the longitudinal axis of rotation of foam cell 10. These centralizer walls aid in both centralizing and stabilizing the high foam generating cell insert 20 within the foam cell 10 as the foaming liquid medium passes therethrough. It should also be noted however, that any number of centralizer walls, as well as cylindrically shaped walls may be employed without departing from the spirit or scope of the invention.

A liquid medium agitator is carried by centralizer walls 22 and 22' at a lower end of foam cell insert 20, the agitator being a cup member 26. The cup member 26 is adapted to receive a foamable liquid medium being introduced into the foam cell 10 and passing between centralizer walls 22 and 22'. In one embodiment, the length of the cup member 26 is about 20 cm with the diameter of the cup member 26 being less than the latitudinal distance between the centralizer walls 22 and 22', so that the cup member 26 can be fixedly attached to interior sides 28 and 28' of the centralizer walls 22 and 22'. It should be noted however, that while the cup member 26 is shown attached to the centralizer walls 22 and 22' in this manner, it is understood that the cup member 26 may also be the same in diameter as the latitudinal distance between the centralizer walls 22 and 22' so that if foam cell insert 20 were injection molded into one piece, for example, the cup member 26 would begin where the centralizer walls 22 and 22' end. The outer diameter of cup member 26 is preferably from about 2 cm to about 6 cm, while the inner diameter is preferably from about 1.5 cm to about 4.5 cm. The inner and outer diameters of the cup member 26, as well as its length which is preferably about 20 cm, depends on the foaming properties of the foamable liquid medium being tested. A high foaming liquid medium may require the use of a cup member having greater inner and outer diameters and length so that the foam being formed in cup member 26 flows out of the cup member 26, and into foam cell 10 at a slower rate. This enables the defoaming or antifoaming agent being introduced into the foam cell 10 to be more accurately tested. The converse, with respect to the geometry of cup member 26, is true when low foaming liquids are being tested. In any event, the diameter of the cup member 26 must be less than that of the foam cell 10, so that an annular opening (not shown) is formed between the exterior of the cup member 26 and the interior of the foam cell 10. The purpose of the annular opening is so that liquid medium can escape from the cup member 26 into the foam cell 10 at which time it is discharged through the outlet port 14 via the outlet conduit 15 and recirculated back into the foam cell 10, thus providing a dynamic liquid testing system. Multiple apertures 32 and 32' may also be provided, but are not necessary, to further enhance the escape of liquid medium from the cup member 26 into foam cell 10 for recirculation.

In order to further stabilize the foam cell insert 20 within the foam cell 10 during use, stabilizer members 30 and 30' are provided at the bottom portion of cup member 26. In the embodiment shown in FIG. 1(b), stabilizer members 30 and 30' extend radially from a lower end of the cup member 26. It should be understood however, that while these stabilizer members 30 and 30' are shown as being baffle-like and are located at a lower end of the cup member 26, these stabilizer members can be located anywhere along the foam cell insert 20, including along the length of the foam cell insert 20 if they are integrally connected to the centralizer walls 22 and 22', provided the centralizer walls 22 and 22' run the entire length of the foam cell insert 20.

There is shown in FIG. 1(c) yet another embodiment of the present invention, that being a low foam generating cell insert 21 used to evaluate high foaming liquid medium. In this embodiment, the liquid agitator comprises a disc-like end member 38 attached at a lower end of and carried by the centralizer walls 22 and 22'. In this embodiment, the diameter of the end member 38 is greater than the latitudinal distance between the centralizer walls 22 and 22'. In one embodiment, the diameter of the disc member is about 4 cm. However, the diameter may vary, depending on the inner diameter of the foam cell 10 being employed. The centralizer walls 22 and 22' are shown spaced at 180 degree angles relative to the longitudinal axis of rotation of the foam cell 10. Again, it should be noted that any number of opposing centralizer walls may be employed without departing from the spirit of the invention.

An aperture 39 is provided in end member 38 for further enhancing the escape of liquid medium into foam cell 10 for recirculation. However, multiple apertures, or none at all may similarly be employed.

Stabilizer members 30 and 30' are shown fixedly mounted to the annular seat member 24 at an upper end of the foam cell insert 21. The stabilizer members 30 and 30' are shown as being arcuate-shaped. It should be understood, however, that any shaped stabilizer members may be employed, without departing from the spirit of the invention.

Figure 2:
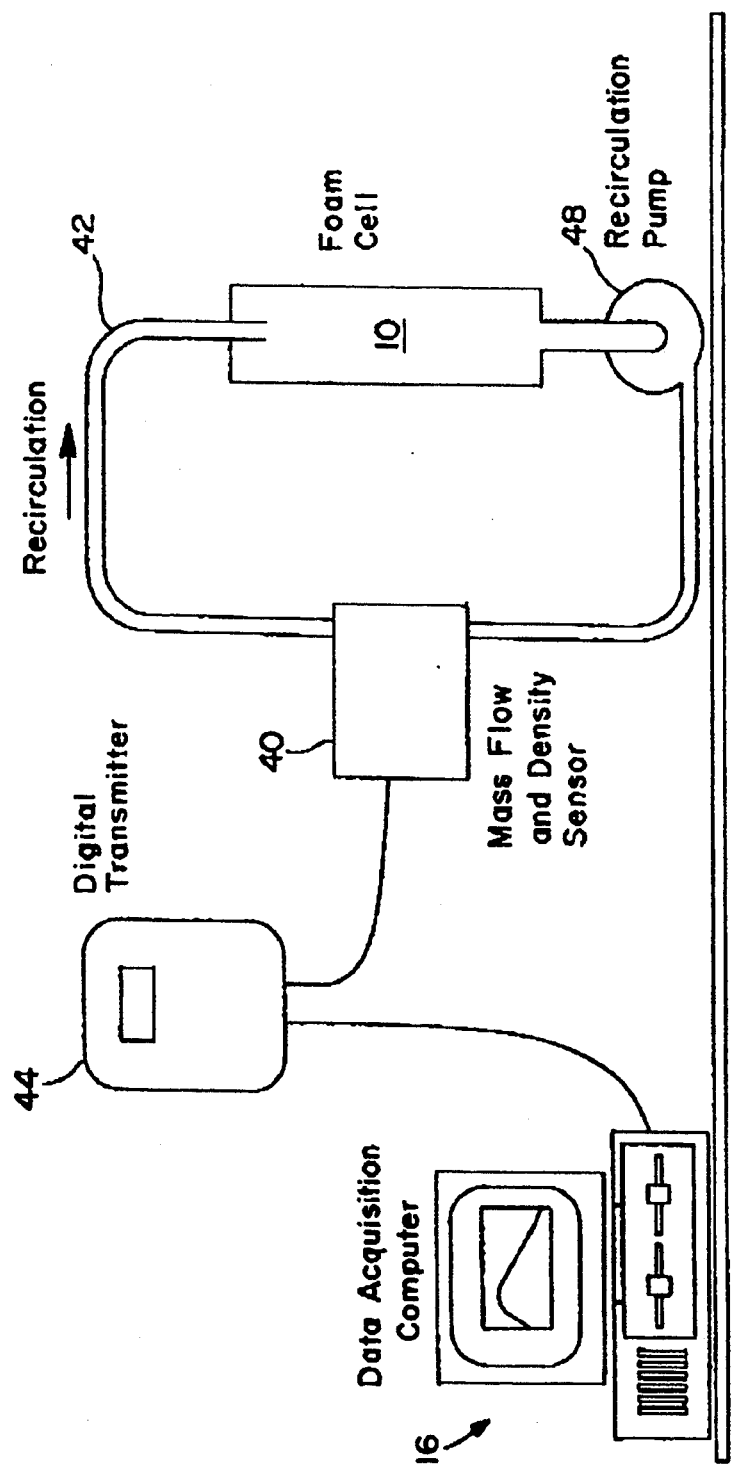
FIG. 2 is a block diagram of the apparatus.

In a preferred embodiment, best seen in FIG. 2, an in-line mass flow and density Sensor 40 is connected to liquid delivery means 42 for measuring the amount of entrained air present in the system. This sensor can in turn be adapted to a digital transmitter 44 and data acquisition computer 46 so that any entrained air measurements can be obtained in analyzable form from the computer 46. The presence of an in-line density sensor has been found to provide entrained air data in addition to usual visual observations in the use of the defoamer testing apparatus of this invention. Entrained air is actually a greater concern than surface foam in many process defoamer/antifoam applications. Thus, the presence of an in-line density sensor offers one the advantage of being capable of quantifying entrained air in addition to, or instead of, surface foam measurements. In addition, it is possible to automate density data acquisition with such a system since the density sensor may be a microprocessor-based instrument as shown in FIG. 2.

The foamable liquid medium is provided by an exterior liquid source (not shown) whereby it is introduced into the foam cell apparatus via recirculation pump 48. Pump 48 then introduces the foamable liquid medium into both foam cell 10 and foam cell insert 20 or foam cell insert 21 simultaneously first by way of liquid delivery means 42, which in turn is connected to spout member 36. The foamable liquid medium then passes through either foam cell insert 20 or 21, depending on which type of foamable liquid medium is being employed, at which time it is agitated through contact with either cup member 26 or end member 38, depending on which foam cell insert is employed.

In operation, depending on the type of foamable liquid medium being employed, i.e., high or low foaming liquid, an appropriate foam cell insert is chosen and disposed within foam cell 10. Foamable liquid medium is introduced from an exterior source through fluid delivery means 42 to spout member 36. Through spout member 36 it is simultaneously deposited into both the foam cell and through the foam cell insert in between centralizer walls 22 and 22'. As it travels through foam cell insert 20 or 21 it comes into contact with the agitator carried by the centralizer walls 22 and 22'. If the agitator is cup member 26, the agitation of the liquid medium entering into the cup member 26 causes the liquid medium to foam. Excess liquid exits the cup member 26 through both apertures 32 and 32' and by overflowing out of the cup member 26. The excess liquid then passes through the annulus (not shown) between the exterior of the cup member 26 and the interior of the foam cell 10 to the bottom of foam cell 10. The excess liquid medium is then discharged from the foam cell 10 via outlet port 14 and through outlet conduit 15 (FIG. 1(a)). The discharged liquid medium is then recirculated back into both the foam cell 10 and foam cell insert 20 via liquid delivery means 42 by pump 48. After a sufficient amount of foam has been formed in foam cell 10, but while the pump 48 continues to recirculate the liquid medium, thus providing a dynamic fluid system, a defoaming or antifoaming agent is introduced into the foam cell 10 through injection aperture 16 (FIG. 1(a)). Measurements are then taken to determine how much foam has been dispersed and for how long the formation of additional foam is inhibited in order to determine the effectiveness of the agent as either a defoamer or antifoam agent. The measurements are made by reading the graduated scale 13 located on foam cell 10 to see how far the level of foam present in foam cell 10 dropped after the agent was introduced. The measurements are taken over various time periods.

Conversely, when testing a high foaming liquid medium, such as black liquor, foam cell insert 21 of FIG. 1(c) is employed. Foam cell insert 21 is disposed within foam cell 10 in the same manner as foam cell insert 20. The process is run in the same manner as previously described except that agitation and consequent foaming of the liquid is provided by end member 38. This agitation causes the foamable liquid medium to foam. After a sufficient amount of foam is formed, the defoaming agent to be tested is introduced into foam cell 10 and evaluated in the same manner as disclosed above.

According to the method aspect of the invention, an interchangeable foam cell insert of varied geometry is chosen and disposed within a foam cell. The foam cell is provided with an inlet port for introducing a liquid medium into both the foam cell and the foam cell insert, and is also provided with an outlet port for discharging the liquid medium after it passes through both the foam cell and the foam cell insert. The foam cell insert is provided with a plurality of centralizer walls extending longitudinally into the foam cell. An agitating member is provided which is carried by the centralizer walls to promote agitation and resultant foaming of a liquid medium which comes into contact with the agitator member. The foam cell insert is provided with a seat or support member which both supports and suspends the foam cell insert within the foam cell. The support member is removably placed over the inlet port of the foam cell. Varyingly configured agitator members are provided for facilitating varying degrees of agitation of a liquid medium.

Once the appropriate foam cell insert is in place within the foam cell, liquid medium is first introduced and then recirculated through both the foam cell and foam cell insert. As the liquid medium comes into contact with the agitator member carried by the centralizer walls of the foam cell insert, it is agitated and foams. Once a sufficient amount of foam is formed within the foam cell, a defoaming or antifoaming agent is then introduced into the foam cell. Its effect on the foam is then measured by viewing the height of the foam before and after the agent was introduced.

The defoamer testing apparatus may be constructed from any suitable material such as glass, but is preferably made from a plastic material such as clear acrylic, polycarbonate or acrylonitrile butadiene-styrene and provided with a suitable case or container containing all the basic components to provide a clean, professional looking test kit. The use of plastic construction materials reduces or eliminates handling and breakage problems associated with glass construction. In addition, the apparatus may be provided with a ground fault interrupt circuit breaker or an "outdoor" switch to reduce the chance of electric shock. A flow regulating valve may also be present in the apparatus to vary the recirculation rate, and hence the rate of foam generation in the foam cell. When present, the flow regulating valve may be connected to the pump outlet. Further, for testing extremely foamy process liquids like Kraft pulp mill black liquor, the defoamer testing apparatus may be equipped with a diverter insert or plate above the normal liquid level. Such a diverter or baffle prevents the recirculating flow from forcing air directly into the pump inlet which would cause the centrifugal pump to cavitate.

Figure 3A:
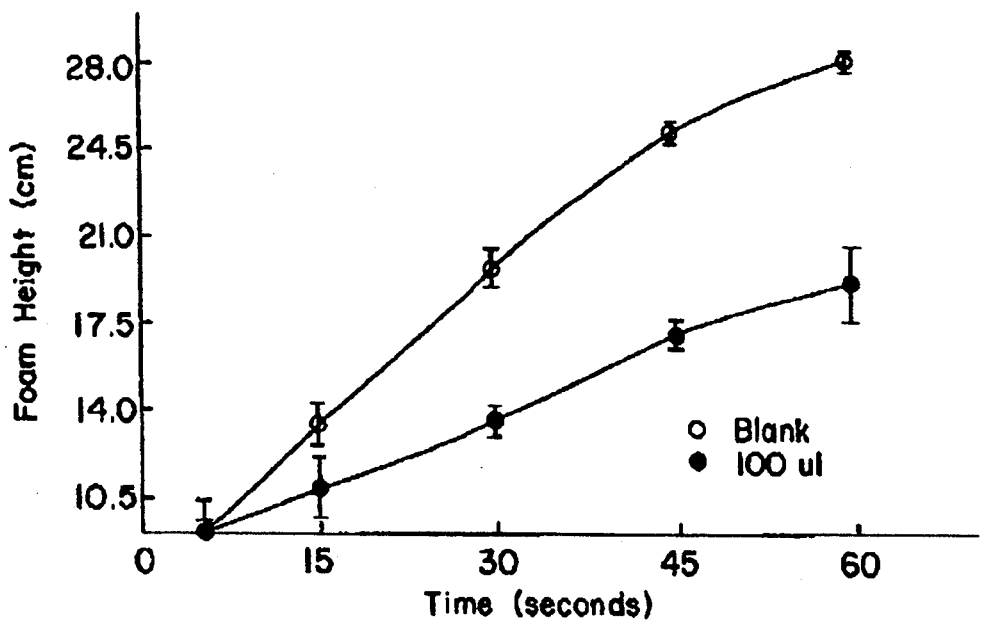
FIG. 3 illustrates surface foam and specific gravity data taken during an antifoam test in accordance with this invention.
Figure 3B:
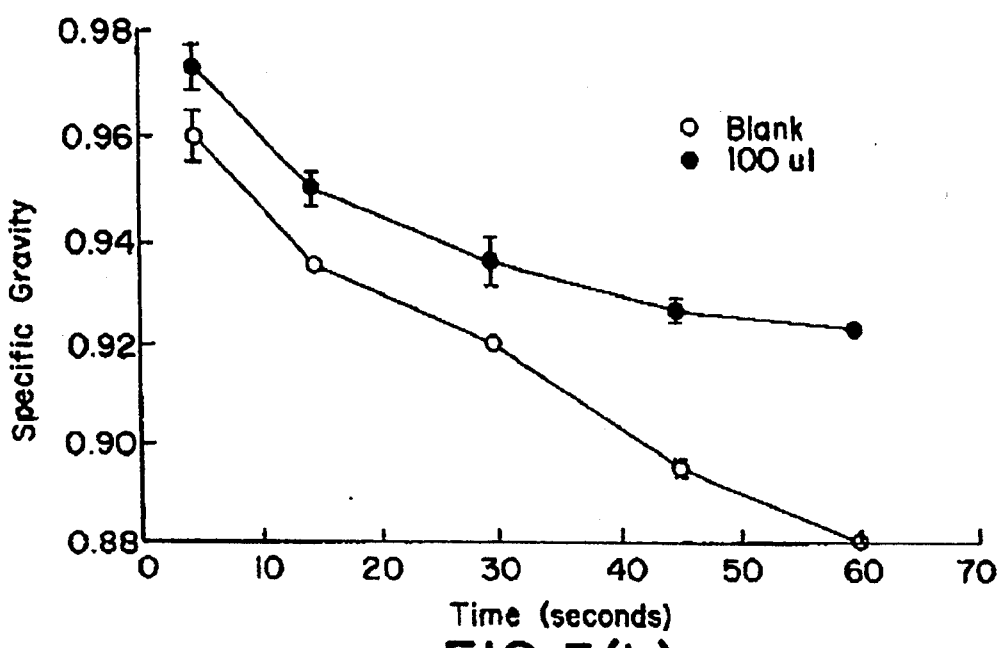

FIG. 3 illustrates specific gravity data (inversely proportional to entrained air content) taken simultaneously with surface foam observations using the defoaming test apparatus and procedure of this invention. It should be noted that the liquid medium specific gravity increases as surface foam is knocked down following the injection of defoaming agent to the testing apparatus at the time of zero seconds. In FIG. 3, the defoaming test was conducted at about 100° F.

Figure 4A:
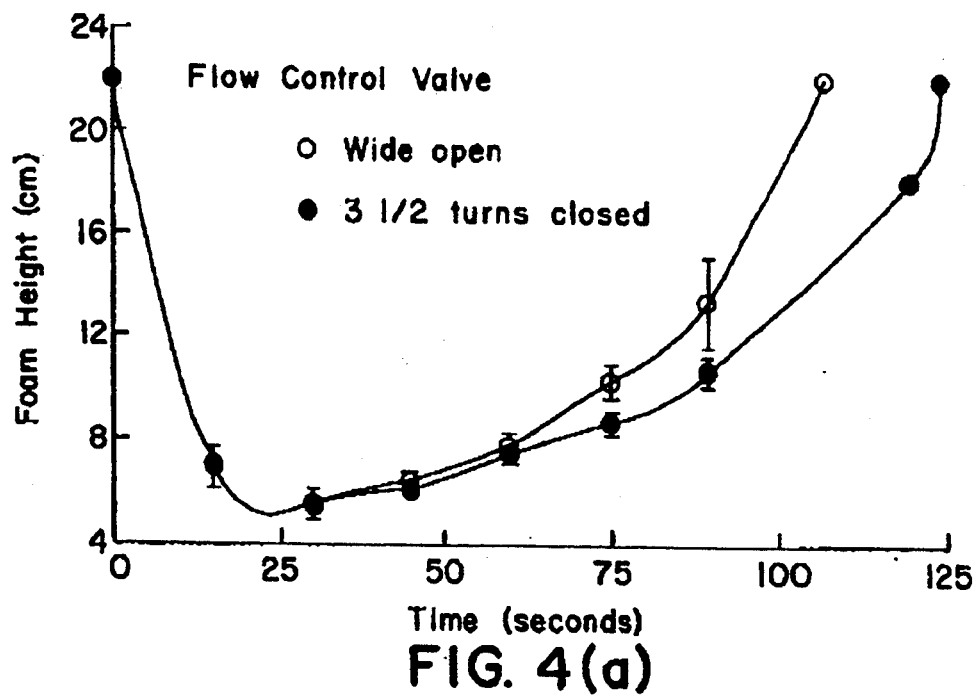
FIG. 4 illustrates surface foam and specific gravity data taken during a defoaming test in accordance with this invention.
Figure 4B:
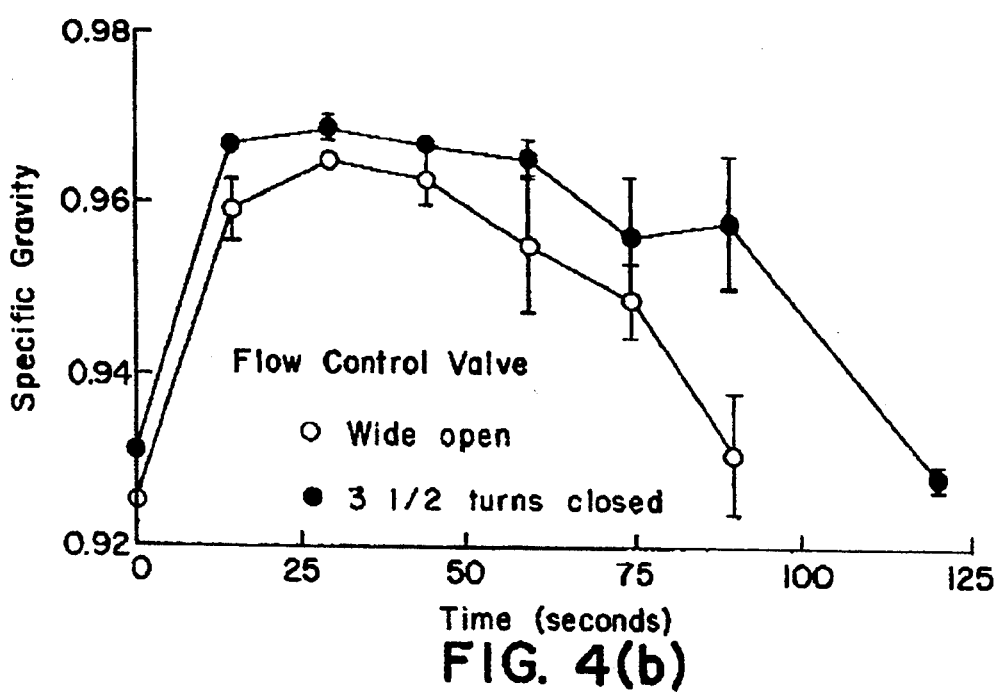

FIG. 4 illustrates surface foam and specific gravity data taken in an antifoaming performance evaluation. In this case, antifoam was added to the liquid medium before foam generation was started, i.e., at the time of zero seconds. The test was conducted at about 110° F. with the flow control valve wide open and also with the flow control valve closed 3½ turns.

Figure 5:
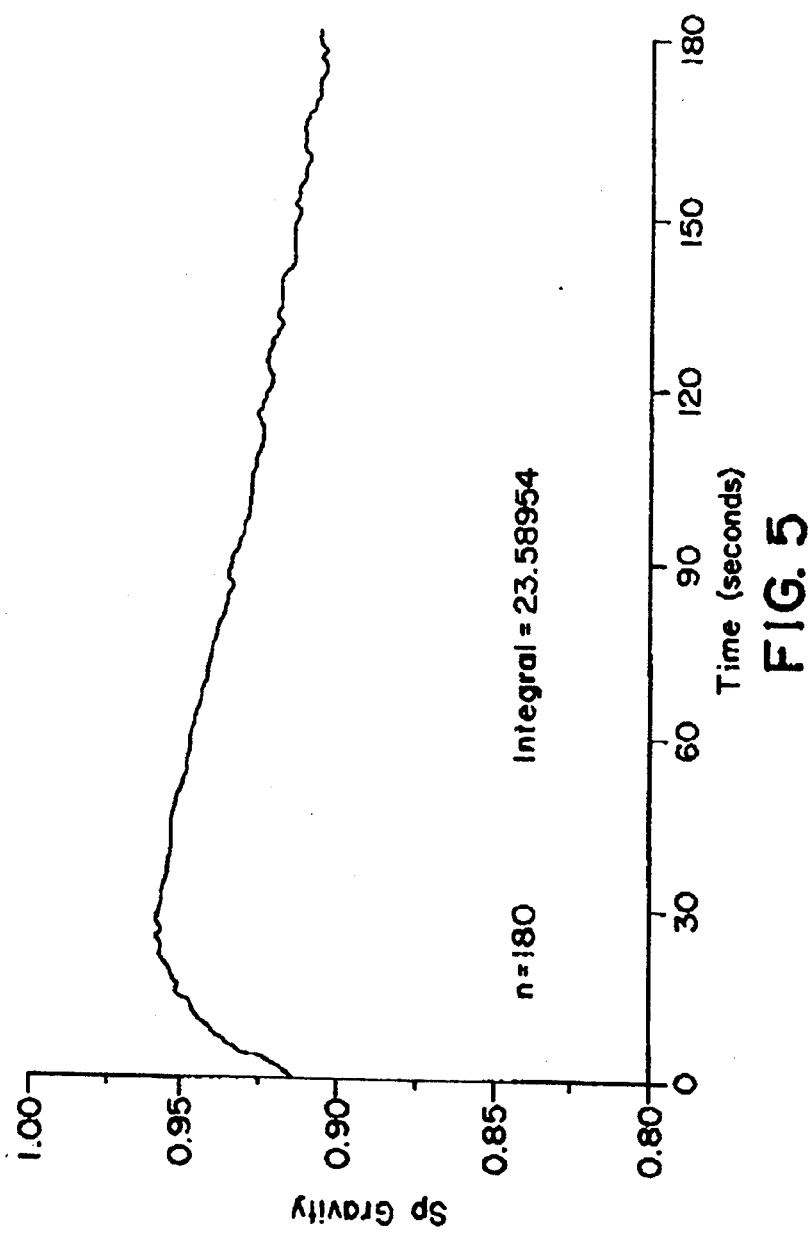
FIG. 5 illustrates a defoaming test in accordance with this invention wherein a computer was used to measure specific gravity of a liquid medium.

FIG. 5 illustrates a defoaming test wherein a computer was used to measure specific gravity of a liquid medium versus time conducted at about 120° F.

It will be recognized by those skilled in the art that changes may be made to the above-described embodiment of the invention without departing from the broad inventive concepts thereof. It is understood, therefore, that this invention is not limited to the particular embodiments disclosed, but is intended to cover all modifications which are within the spirit and scope of the invention as defined by the appended claims.

What is claimed is:

1. An apparatus for measuring the foam inhibiting effectiveness of a defoaming or antifoaming agent on various types of foamable liquids utilizing a single foam cell wherein a liquid medium is first introduced into, and then recirculated through the foam cell, after which the defoaming or antifoaming agent to be tested is introduced into the foam cell for evaluation of its effectiveness, wherein the apparatus comprises:

(a) a generally cylindrical foam cell having an inlet port located at one end of said foam cell for receiving said liquid medium, an outlet port located at a distal end of said foam cell for discharging said liquid medium, and a graduated scale on said foam cell for measuring the height of foam present in said foam cell;

(b) means for supplying said liquid medium into said foam cell through said inlet port;

(c) means for circulating said liquid medium into and out of said foam cell; and (d) means for foaming said liquid medium wherein said means are removably mounted over said inlet port and disposed within said foam cell, said means comprising an interchangeable foam cell insert of varied geometry depending upon the foaming properties of said liquid medium.

2. The apparatus of claim 1 wherein said foam cell insert comprises a plurality of centralizer walls concentrically disposed within said foam cell and extending longitudinally within said foam cell along a central axis of rotation of said foam cell, and wherein a terminal end of said insert is located a predetermined distance above said outlet port of said foam cell.

3. The apparatus of claim 2 wherein said foam cell insert includes means for agitating said liquid medium and causing it to foam, said means for agitating being fixedly attached to said centralizer walls 4. The apparatus of claim 3 wherein said means for agitating said liquid medium comprises a cup member.

5. The apparatus of claim 4 wherein the diameter of said cup member is less than the diameter of said foam cell, thus forming an annulus between interior walls of said cell and exterior walls of said cup member.

6. The apparatus of claim 5 wherein said plurality of centralizer walls comprises three parallel centralizer walls spaced 120 degrees apart around a longitudinal axis of rotation of said cup member.

7. The apparatus of claim 5 wherein said cup member further includes a plurality of apertures located therein for allowing foaming liquid medium to escape into said cell.

8. The apparatus of claim 7 wherein said cup member further includes a plurality of stabilizing members extending radially from said cup member, to both stabilize and centralize said means for foaming within said cell.

9. The apparatus of claim 3 wherein said means for agitating comprises a disc member fixedly attached to said centralizer walls.

10. The apparatus of claim 9 wherein said plurality of centralizer walls comprises two opposing parallel centralizer walls spaced 180 degrees apart around a longitudinal axis of rotation of said disc member.

11. The apparatus of claim 1 further including alignment members extending radially from said means for foaming to maintain alignment of said means for foaming within said foam cell relative to said longitudinal axis of rotation of said foam cell.

12. The apparatus of claim 1 further including means for removably mounting said means for foaming onto said inlet port of said cell.

13. The apparatus of claim 12 wherein said means for removably mounting comprises an annular seat member having at least one aperture located therein through which said liquid medium may be introduced into said foam cell.

14. The apparatus of claim 13 wherein said annular seat member further includes a tube member inserted through said aperture of said annular seat member wherein one end of said tube member is connected to said means for supplying liquid medium.

15. The apparatus of claim 1 further including means for measuring entrained air, said means being integrally connected to said means for supplying liquid medium.

16. The apparatus of claim 15 wherein said means for measuring entrained air comprises an in-line mass flow and density sensor.

17. The apparatus of claim 1 further including means for measuring the temperature within said foam cell.

18. The method of measuring the foam inhibiting effectiveness of a defoaming or antifoaming agent in a foamable liquid medium comprising
   (a) providing a generally cylindrical foam cell having an inlet port located at one end of said foam cell for receiving said liquid medium, an outlet port located at a distal end of said foam cell for discharging said liquid medium, and a graduated scale on said foam cell for measuring the height of foam present in said foam cell;
   (b) introducing said liquid medium into said foam cell through said inlet port;
   (c) circulating said liquid medium into and out of said foam cell;
   (d) providing means for foaming said liquid medium wherein said means are removably mounted over said inlet port and disposed within said foam cell, said means comprising an interchangeable foam cell insert of varied geometry depending upon the foaming properties of said liquid medium;
   (e) introducing a defoaming or antifoaming agent into said foam cell; and
   (f) measuring the reduction in foam present in said foam cell.

19. A method as in claim 18 further including providing alignment members extending radially from said foam cell insert to stabilize said foam cell insert.

20. A method as in claim 18 wherein said foam cell insert comprises a plurality of centralizer walls concentrically disposed within said foam cell and extending longitudinally within said foam cell along a central axis of rotation of said foam cell, and wherein a terminal end of said insert is located a predetermined distance above said outlet port of said foam cell.

21. A method as in claim 20 wherein said foam cell insert includes means for agitating said liquid medium and causing it to foam, said means for agitating being fixedly attached to said centralizer walls.

22. A method as in claim 18 further including providing means for removably mounting said foam cell insert onto said inlet port of said foam cell.

23. A method as in claim 18 including providing means for measuring air entrained in said liquid medium.

24. A method as in claim 18 including providing means for measuring temperature within said foam cell.

* * * * *